(12) United States Patent
Govari et al.

(10) Patent No.: US 12,256,982 B2
(45) Date of Patent: Mar. 25, 2025

(54) MEASURING THICKNESS OF CARDIAC WALL TISSUE DURING ABLATION

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 834 days.

(21) Appl. No.: 16/823,527

(22) Filed: Mar. 19, 2020

(65) Prior Publication Data

US 2021/0290301 A1    Sep. 23, 2021

(51) Int. Cl.
A61B 18/14    (2006.01)
A61B 18/00    (2006.01)
A61B 90/00    (2016.01)

(52) U.S. Cl.
CPC ............. *A61B 18/1492* (2013.01); *A61B 2018/00351* (2013.01); *A61B 2018/00577* (2013.01); *A61B 2018/00613* (2013.01); *A61B 2018/00839* (2013.01); *A61B 2090/062* (2016.02)

(58) Field of Classification Search
None
See application file for complete search history.

(56) References Cited

U.S. PATENT DOCUMENTS

| | | | |
|---|---|---|---|
| 8,456,182 B2 | 6/2013 | Bar-Tal et al. | |
| 9,918,787 B2 * | 3/2018 | Heimbecher | A61B 90/04 |
| 2003/0144653 A1 | 7/2003 | Francischelli | |
| 2007/0062547 A1 | 3/2007 | Pappone | |
| 2010/0204560 A1 | 8/2010 | Salahieh | |
| 2010/0249771 A1 | 9/2010 | Pearson | |
| 2011/0118727 A1 * | 5/2011 | Fish | A61B 5/01 606/34 |
| 2016/0166309 A1 * | 6/2016 | K V | A61B 18/12 606/32 |
| 2017/0014181 A1 | 1/2017 | Bar-tal et al. | |
| 2017/0151029 A1 * | 6/2017 | Mickelsen | A61M 25/0169 |
| 2018/0043189 A1 * | 2/2018 | Thapliyal | A61B 34/10 |
| 2018/0125575 A1 | 5/2018 | Schwartz | |
| 2019/0038347 A1 | 2/2019 | Panescu | |
| 2020/0107877 A1 * | 4/2020 | Koblish | A61B 5/287 |

(Continued)

OTHER PUBLICATIONS

European Search Report for corresponding EPA No. 211634779 dated Jul. 20, 2021.

(Continued)

*Primary Examiner* — Sean W Collins
*Assistant Examiner* — Nora W Rhodes

(57) ABSTRACT

A method for estimating a thickness of cardiac tissue undergoing ablation includes the steps of (a) applying a sequence of ablation pulses to a region of the cardiac tissue, so as to create a lesion, and (b) for a given ablation pulse in the sequence, an incremental depth added to the lesion due to the given ablation pulse is estimated. A cumulative depth of the lesion is estimated based on the cumulative depth prior to the given pulse, and on the incremental depth. An amplitude of an electrogram signal at the region is assessed after applying the given ablation pulse, and, if the amplitude exceeds a predefined threshold, an estimate of the thickness is set to be at least the cumulative depth.

9 Claims, 2 Drawing Sheets

(56) References Cited

U.S. PATENT DOCUMENTS

2021/0186604 A1    6/2021    Altmann et al.
2022/0079669 A1    3/2022    Panescu et al.

OTHER PUBLICATIONS

Sasaki et al., "Myocardial Structural Associations With Local Electrograms: A Study of Postinfarct Ventricular Tachycardia Pathophysiology and Magnetic Resonance Based Noninvasive Mapping", Circulation: Arrhythmia and Electrophysiology, vol. 5, No. 6, pp. 1081-1090, Dec. 2012.

* cited by examiner

MEASURING THICKNESS OF CARDIAC WALL TISSUE DURING ABLATION

FIELD OF THE INVENTION

The present invention relates generally to cardiac sensing and ablation, and specifically to estimating properties of cardiac wall tissue undergoing ablation.

BACKGROUND OF THE INVENTION

A number of methods may be used to estimate a thickness of a cardiac wall, such as ultrasound, fluoroscopy, and MRI imaging. The estimated wall thickness may be further correlated with electrophysical signals to estimate an injury of the cardiac wall tissue. For example, Takeshi Sasaki et al. describe in "Myocardial Structural Associations with Local Electrograms: A Study of Post-Infarct Ventricular Tachycardia Pathophysiology and Magnetic Resonance Based Non-Invasive Mapping," Circulation Arrhythmia and Electrophysiology, December, 2012; 5(6): 1081-1090, significant associations between left ventricular wall thickness, post infarct scar thickness, and intramural scar location seen in MRI, and local endocardial electrogram bipolar/unipolar voltage, duration, and deflections on electroanatomical mapping.

SUMMARY OF THE INVENTION

An embodiment of the present invention provides a method for estimating a thickness of cardiac tissue undergoing ablation, includes the steps of (a) applying a sequence of ablation pulses to a region of the cardiac tissue, so as to create a lesion, and (b) for a given ablation pulse in the sequence, an incremental depth added to the lesion due to the given ablation pulse is estimated. A cumulative depth of the lesion is estimated based on the cumulative depth prior to the given pulse, and on the incremental depth. An amplitude of an electrogram signal at the region is assessed after applying the given ablation pulse, and, if the amplitude exceeds a predefined threshold, an estimate of the thickness is set to be at least the cumulative depth.

In some embodiments, the method further includes terminating the sequence of ablation pulses in response to detecting that the amplitude of the electrogram signal is below a predefined value. In some embodiments, the predefined value is equal to the predefined threshold.

In an embodiment, assessing the amplitude of an electrogram signal includes measuring the amplitude during an intermission between the ablation pulses. In another embodiment, the steps are performed automatically under a processor control.

In some embodiments, applying the sequence of ablation pulses includes planning the sequence such that an expected incremental depth is smaller than a prespecified incremental value.

In some embodiments, the method further includes, after setting the estimate of the thickness, changing the sequence of ablation pulses to change the incremental depth caused by a next ablation step.

In an embodiment, assessing the amplitude of the electrogram signal includes measuring the electrogram signal using the same electrodes used for applying the ablation pulses. In another embodiment, applying the ablation pulses includes applying irreversible electroporation (IRE) pulses.

In yet another embodiment, applying the ablation pulses includes applying radiofrequency (RF) ablation.

There is further provided, in accordance with another embodiment of the present invention, a system for estimating a thickness of cardiac tissue undergoing ablation. The system includes an interface and a processor. The interface is configured to output a sequence of ablation pulses for a probe to apply to a region of the cardiac tissue, so as to create a lesion. The processor is configured, for a given ablation pulse in the sequence, to (i) estimate an incremental depth added to the lesion due to the given ablation pulse, (ii) estimate a cumulative depth of the lesion based on the cumulative depth prior to the given pulse, and on the incremental depth, and (iii) assess an amplitude of an electrogram signal at the region after the probe applying the given ablation pulse, and, if the amplitude exceeds a predefined threshold, set an estimate of the thickness to be at least the cumulative depth.

BRIEF DESCRIPTION OF THE DRAWINGS

The present disclosure will be more fully understood from the following detailed description of the embodiments thereof, taken together with the drawings, in which.

DETAILED DESCRIPTION OF EMBODIMENTS

Overview

Figure 1:
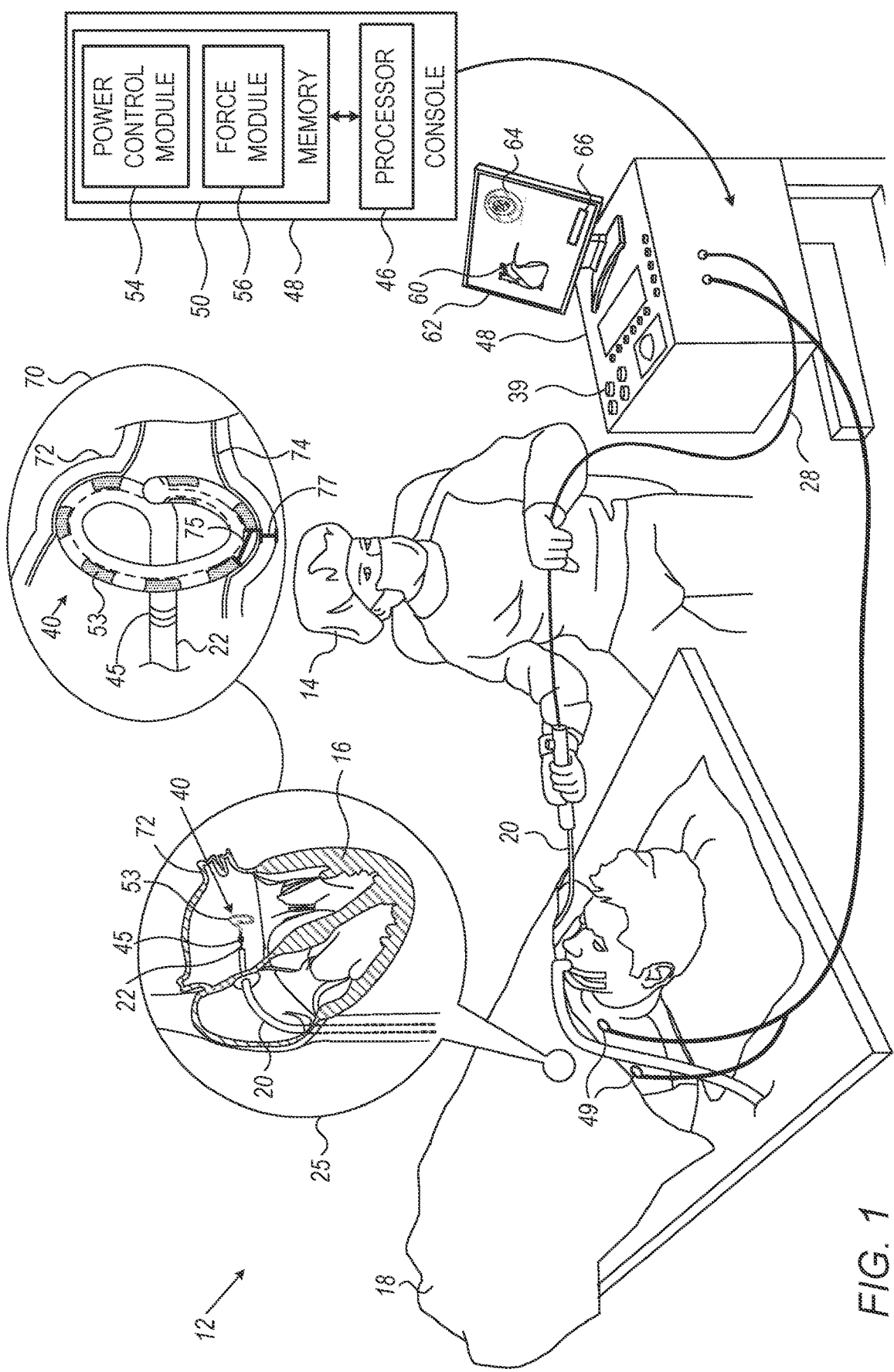
FIG. 1 is a schematic, pictorial illustration of a catheter-based system for irreversible electroporation (IRE) treatment and electrogram sensing, in accordance with an exemplary embodiment of the present invention.

A lesion in cardiac tissue of a patient undergoing an ablative procedure may be formed using irreversible electroporation (IRE), or using other types of ablative energy, such as radiofrequency (RF), which can be applied using a catheter. In IRE ablation, the catheter is maneuvered such that electrodes disposed on a distal end of the catheter are in contact with the tissue. Then, high voltage bipolar pulses are applied between the electrodes, and strong electric field pulses produced in tissue cause cell death and production of the lesion. In RF ablation, an alternating RF current is applied to the tissue by one or more electrodes, causing cell death by heat.

Estimation of wall thickness at a tissue location undergoing ablation may be important to avoid severe side effects of the ablation, such as perforation of the cardiac wall. Additionally, the estimation can assist in shortening the ablative procedure with nearby locations ablated more rapidly using the estimated wall thickness as a baseline estimation at these locations. As indicated in the Background, various imaging methods can be used to measure cardiac wall thickness. Using such methods during an ablation procedure; however, adds substantial complexity to the ablating system and to the clinical workflow.

Exemplary embodiments of the present invention that are described hereinafter provide systems and methods for real time acquisition and analysis of electrograms from cardiac tissue to estimate the thickness of the wall tissue undergoing ablation. The disclosed systems may apply an automatic stepwise ablation/estimation process to achieve an increasingly refined estimation that, in turn, can be used to achieve an optimal lesion depth (e.g., minimal lesion depth sufficient to eliminate an arrhythmia).

In some exemplary embodiments, catheter ablation electrodes, such as IRE or RF ablation electrodes, are further used to acquire electrograms. In other exemplary embodiments, other kinds of ablative energy (e.g., laser, cryogenic) are applied using a catheter, with other sensing electrodes disposed on the catheter used to acquire electrograms. In general, any catheter-based ablation method that creates lesions in tissue, with a depth that can be modeled as a function of an ablation time duration, can be used with the disclosed ablation/estimation process.

In an exemplary embodiment, the disclosed ablation/estimation process begins with a physician operating a processor-controlled system to ablate tissue during a given time duration to produce a lesion of a prespecified planned depth, with the required time duration estimated using one of the above-mentioned lesion-depth models relevant to the method of ablation. Electrodes are then used to detect electrogram signals from the ablated tissue. For IRE and RF ablation, electrogram detection may be done using the same electrodes.

If the measured electrogram signals have an amplitude above a prespecified threshold value, the processor determines that tissue thickness is at least as thick as the prespecified lesion depth (i.e., the processor sets a lower bound for the thickness). In such a case, the processor directs the application of an additional time duration to ablate tissue to increase lesion depth by an incremental amount, and, subsequently, to acquire electrograms to re-estimate an accumulated lesion depth. The above steps can be repeated until an amplitude of the electrogram signal falls below the prespecified threshold value.

Thus, as the disclosed ablation/estimation process progresses, the lower bound for the estimated wall thickness gradually grows (as this lower bound equals the accumulated lesion depth in tissue that still has an electrogram signal above the prespecified threshold cardiac wall tissue). Eventually the amplitude of the electrogram signal drop below the prespecified threshold. At that point in the process, the processor estimates the wall tissue thickness to be the accumulated lesion depth that caused the signal amplitude to drop, and responsively terminates the ablation at the location.

The physician controls the estimation accuracy by selecting the additional time duration to be such that planned incremental lesion depth is smaller than a prespecified incremental value that is considered safe.

As noted above, the above described stepwise ablation/estimation process may be performed, in its entirety, under automatic processor control. Therefore, in practice, the physician and the patient both experience the disclosed step-wise ablation/estimation process as a single continuous ablation process (including the intermissions required for electrogram acquisitions).

The disclosed stepwise ablation/estimation technique allows the use of an uneven number of ablation and estimation steps, by for example, estimating thickness every varying number of ablative energy pulses. Accordingly, in an exemplary embodiment, a method for estimating a thickness of cardiac tissue undergoing ablation is provided, the method including applying a sequence of ablation pulses to a region of the cardiac tissue, so as to create a lesion, and, for a given ablation pulse in the sequence (a) estimating an incremental depth added to the lesion by the given ablation pulse, (b) estimating a cumulative depth of the lesion based on the cumulative depth prior to the given pulse, and on the incremental depth, (c) and assessing an amplitude of an electrogram signal at the region after applying the given ablation pulse, and, if the amplitude exceeds a predefined threshold, setting an estimate of the thickness to be at least the cumulative depth.

In some exemplary embodiments, the physician or the processor may terminate the sequence of ablation pulses in response to detecting that the amplitude of the electrogram signal is below a predefined value which is different than the predefined threshold.

In the present context, applying a pulse of an ablative energy includes also applying non-electrical energies for a given duration, such as cryogenic and laser energies.

By estimating the thickness of cardiac wall tissue undergoing ablation using an already available capability to acquire and analyze electrograms, accurate and cost effective ablative treatments may be possible.

System Description

FIG. 1 is a schematic, pictorial illustration of a catheter-based system 12 for irreversible electroporation (IRE) treatment and electrogram sensing, in accordance with an exemplary embodiment of the present invention. The IRE procedure is performed by a physician 14, and, by way of example, the procedure in the description hereinbelow is assumed to comprise IRE of a portion of a myocardium 16 of the heart of a human patient 18.

In order to perform the ablation, physician 14 inserts a probe 20, by way of example, a Lasso® catheter (made by Biosense Webster, Irvine, Calif.) into a lumen of the patient, so that a distal end 22 of probe 20 enters the heart of the patient. As insets 25 and 70 show, distal end 22 comprises multiple electrodes 53 mounted on the outside of an arcuate section 40 (e.g., Lasso section 40) of distal end 22, the electrodes 53 contacting a location of the myocardium. Electrodes 53 are spaced one from the other by a distance 75, d. Distal end 22 also comprises a force sensor 45, and probe 20 also comprises a proximal end 28.

System 12 is controlled by a system processor 46, which is located in an operating console 48 of the apparatus. Console 48 comprises controls 39 which are used by physician 14 to communicate with the processor 46. During the procedure, processor 46 typically tracks a location and an orientation of distal end 22 of the probe, using, for example, a magnetic tracking method, wherein magnetic transmitters external to patient 18 generate signals in coils positioned in the distal end. The Carto® system produced by Biosense-Webster uses such a tracking method. As another example, a location and an orientation of distal end 22 may be tracked using the Advanced Catheter Location (ACL) system, made by Biosense-Webster, which is described in U.S. Pat. No. 8,456,182, whose disclosure is incorporated herein by reference. In the ACL system, a processor estimates the respective locations of multiple electrodes 53 based on impedances measured between each of electrodes 53, and a plurality of surface electrodes 49 that are coupled to the skin of patient 18.

The software for processor 46 may be downloaded to the processor in electronic form, over a network, for example. Alternatively or additionally, the software may be provided on non-transitory tangible media, such as optical, magnetic, or electronic storage media. The tracking of distal end 22 is typically displayed on a three-dimensional representation 60 of the heart of patient 18 on a screen 62. The progress of the IRE treatment performed with apparatus 12 (e.g., an accumulated lesion depth) is typically also displayed on screen 62, as a graphic 64 and/or alphanumeric data 66.

As inset 70 shows, Lasso section 40 accepts the shape of an ostium 72 tissue of PV 74 anatomy while pushing tissue hard enough to have hemi-cylinder-shaped electrodes 53 firmly in contact with ostium 72 wall tissue over most or an entirety of electrodes 53 area, i.e., with minimal, if any, electrode area left exposed to blood. Ostium 72 wall tissue that undergoes IRE ablation by electrodes 53 has a local thickness D, 77, which is estimated in some of the disclosed exemplary embodiments of the present invention, for example, using interelectrode distance 75 and a voltage drop between adjacent electrodes 53.

In order to operate system 12, processor 46 communicates with a memory 50, which has a number of modules used by the processor to operate the apparatus. Thus, memory 50 comprises a power-control module 54 and a force module 56. Power-control module 54 delivers IRE power to electrodes 53, and also measures the instantaneous power, typically by measuring the instantaneous RMS voltage over an electrode pair.

Force module 56 measures an instantaneous contact force by acquiring and evaluating signals from force sensor 45 in distal end 22. In an exemplary embodiment, based on the instantaneous voltage and contact force, processor 46 estimates time-dependent lesion depth 77. A system and method to estimate lesion depth as a function of IRE ablation time duration are described in U.S. patent application Ser. No. 16/726,312, filed Dec. 24, 2019, titled "Calculating an Irreversible Electroporation (IRE) Index Taking IRE Field, Contact Force and Time Into Account," which is assigned to the assignee of the present patent application, which document is incorporated by reference.

In another exemplary embodiment, RF ablative energy is applied, and a time-dependent lesion depth 77 is estimated, by the processor using measured instantaneous current and contact force. A system and method to estimate lesion depth as a function of RF ablation time duration are described in U.S. Patent Application Publication 2017/0014181, which document is incorporated by reference.

Memory 50 may also comprise other modules, such as a temperature-sensing module and an irrigation module. For simplicity, other such modules are not described in this application. The modules of memory 50 may comprise hardware as well as software elements.

Measuring Thickness of Cardiac Wall Tissue During Ablation

Figure 2:
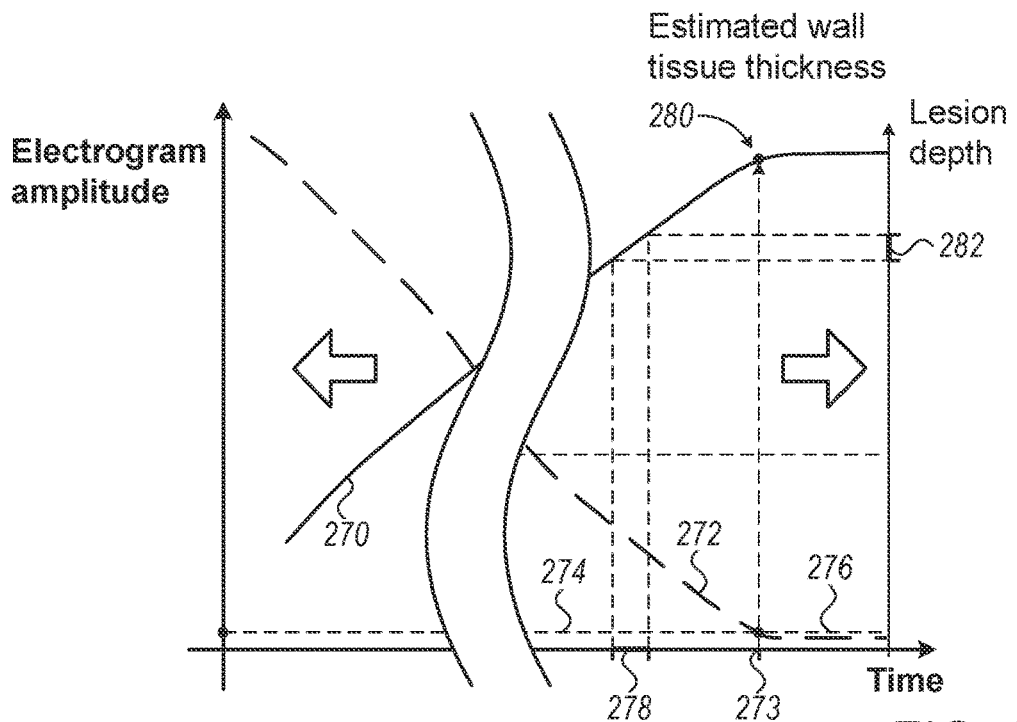
FIG. 2 is a graph schematically showing lesion depth and electrogram signal amplitude at the location of the lesion as a function of ablation time duration, according to an exemplary embodiment of the present invention.

FIG. 2 is a graph that schematically shows lesion depth and electrogram signal amplitude at the location of the lesion as a function of ablation time duration, according to an exemplary embodiment of the present invention. As seen, over a major portion of the shown lesion-depth vs. ablation-time curve 270, the lesion depth increases monotonically, usually with a weak nonlinearity. At the same time, an amplitude 272 of the electrogram from the ablated location diminishes as a lesion is formed at deeper depths. At a certain time 273 during the ablation, the lesion goes as deep as the tissue wall thickness and the amplitude of the electrogram falls below a prespecified threshold value 274.

Exemplary embodiments of the present invention enable a physician to estimate a respective thickness 280 i.e., essentially tissue wall thickness at the ablated arrhythmogenic location. In an exemplary embodiment, the physician ablates, using, for example, electrodes 53 of lasso catheter 20, the cardiac tissue location over a given time duration to form a lesion in tissue to a planned depth smaller than depth 280. Based on the methods discussed in FIG. 1, the processor of the ablation system can estimate a resulting lesion depth. Next, during an intermission in ablation, the processor receives an electrogram signal from the ablated location, using, for example, the same electrodes 53 of probe 20.

In most cases some electrophysiological-active tissue remains at the location, and the amplitude of the electrogram signal would initially be above the prespecified threshold value. Therefore, the processor estimates tissue thickness to be, at minimum, the depth of the lesion, though this initial depth is usually underestimated. The stepwise ablation/estimation process repeats, either under control of the processor, or manually by the physician, where, at each step of the process, tissue is further ablated for an additional time duration, such as duration 278, to add an incremental lesion depth 282 which the processor estimates as to its value and accumulated lesion depth. In an exemplary embodiment, the value of the additional time duration is selected such that the planned incremental lesion depth is smaller than a prespecified incremental value, so as not to over-ablate tissue and/or to achieve accurate estimation of the wall thickness.

An example of an RF ablation settings that may be used for ablating an incremental lesion depth (less than 2 mm) is given by Table I:

RF Low Depth Parameters:

TABLE I

| Parameter | Range |
| --- | --- |
| Preset RF ablative energy | 270J-540J (Typically 360J) |
| Maximum RF power level | 90 W |
| Power range | 0-90 W |
| Allowable temperature range | 45-65° C. (typically 50° C.) |
| Allowable irrigation flow rate | 4-15 ml/min |
| Maximal ablation time | 3-6 Sec (Typically 4 sec) |

An example of an IRE ablation settings that may be used for ablating an incremental lesion depth (less than 3 mm) is given by Table II:

IRE Low Depth Parameters:

TABLE II

| Parameter | Range |
| --- | --- |
| Preset IRE Electrical Field | 500 V/cm-1000 V/cm |
| Pulse width | 0.5-5 mSec |
| Delay between trains | 1 ms-1000 ms |
| Number of pluses in Train | 5-20 |
| Number of Trains | 1-90 |

The ablation and subsequent wall tissue thickness estimation steps can be applied with finer incremental lesion depths, e.g., of less than a millimeter, depending on the value of the additional time duration selected for a repeated ablation, or on other parameters, such as RF power or IRE peak voltage used with the aforementioned lesion-depth models.

Again, immediately after the ablation step, the processor receives an electrogram signal from the ablated location and estimates tissue wall thickness as follows. If the electrogram signal amplitude is below a prespecified amplitude 276 (For example below 0.1 mV), the processor re-estimates tissue thickness at the ablated location to be the accumulated depth of the lesion, and terminate the ablation at the location.

If, on the other hand, the electrogram signal amplitude is still above the prespecified amplitude 276, the processor updates the estimation to be, at minimum, the newly accumulated depth of the lesion. The processor or the physician can then repeat the ablation steps for an additional time duration 278 and then estimate an incremental lesion depth 282 and measure electrogram signals. As the arrhythmogenic signal gradually decreases from step to step, the estimated tissue thickness becomes more accurate.

The disclosed technique enables the halting of tissue ablation after thickness 280 has been determined, which otherwise may result in hazard to nearby organs and even in perforation. Moreover, further ablation has no clinical value, as at time 273 tissue has practically ceased being arrhythmogenic.

The above described stepwise ablation/estimation process may be performed automatically, and in practice be experienced as a single continuous ablation, including the typically few intermissions required for electrogram acquisition.

The process described in FIG. 2 is brought purely for purpose of clarity. In practice, actual curves of the disclosed models are used, which are based on a large data base of ablations. The given ablation duration and the additional ablation durations may vary according to the location and type of arrhythmia, and from patient to patient.

Figure 3:
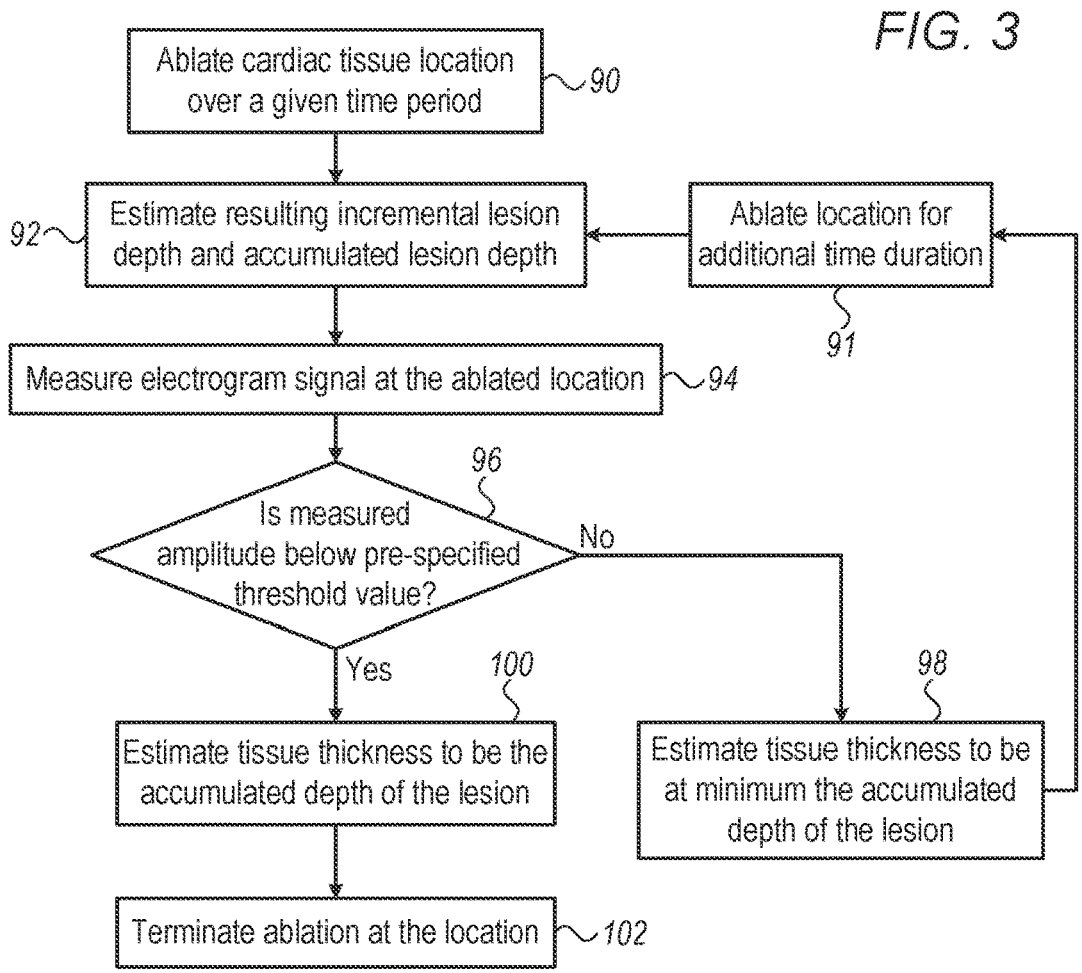
FIG. 3 is a flow chart schematically describing a method for estimating thickness of cardiac wall tissue undergoing ablation using the system of FIG. 1, according to an exemplary embodiment of the present invention.

FIG. 3 is a flow chart schematically describing a method to estimate thickness of cardiac wall tissue undergoing ablation using the system 12 of FIG. 1, according to an exemplary embodiment of the present invention. The algorithm according to the presented embodiment carries out a process that begins with physician 14 ablating a cardiac tissue location over a given time period, at an initial ablation step 90.

At a lesion depth estimation step 92, using a lesion-depth vs. ablation time duration model, such as the models described in FIG. 1, a processor 46 estimates an incremental and accumulated lesion depth. At the first ablation iteration the incremental depth equals the accumulated depth.

Next, using either the same, or a different, catheter, physician 14 measures an electrogram signal at the ablated location, at an electrogram acquisition step 94.

At an electrogram amplitude checking step 96, processor 46 checks if the amplitude (e.g., a peak value or an RMS value) of the electrogram signal is below a prespecified threshold value.

If there is still substantial electrophysiological activity at the ablated location, i.e., electrogram amplitude above the threshold value, processor 46 estimates the ablated cardiac wall thickness, at a tissue wall thickness estimation step 98, to be, at minimum, the accumulated depth of the lesion. The process then returns to step 91 to perform incremental ablation, at an incremental ablation step 91.

Eventually, processor 46 determines that the electrogram amplitude is below the threshold, and then processor 46 estimates the ablated cardiac wall thickness, at a wall tissue thickness estimation step 100, to be the accumulated depth of the lesion. Responsively, processor 46 terminates the ablation at the location, at an ablation termination step 102.

Although the embodiments described herein mainly address cardiac applications, the methods and systems described herein can also be used in other medical applications, such as in neurology, e.g., for monitoring a nerve signal.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for iteratively estimating a thickness of cardiac tissue undergoing ablation, the method comprising the steps of:
   prespecifying a planned depth for ablation and a prespecified incremental value, wherein the prespecified incremental value is less than the planned depth for ablation;
   applying a sequence of ablation pulses to a region of the cardiac tissue, so as to create a lesion; and
   for a given ablation pulse in the sequence:
      estimating a current incremental depth added to the lesion due to the given ablation pulse;
      estimating a cumulative depth of the lesion based on a prior cumulative depth prior to the given pulse, and on the current incremental depth;
      assessing an amplitude of an electrogram signal at the region of the cardiac tissue undergoing ablation after applying the given ablation pulse, and, if the amplitude exceeds a predefined threshold, setting an estimate of the thickness to be at least the last estimated cumulative depth; and
      setting, for a next ablation pulse in the sequence of ablation pulses, an additional time duration for the next ablation where the additional time duration is configured to add a next incremental lesion depth, wherein the next incremental lesion depth is estimated to change a next incremental depth caused by the next ablation pulse to the region of the cardiac tissue to be smaller than the prespecified incremental value;
   wherein applying the ablation pulses comprises applying irreversible electroporation (IRE) pulses,
   wherein the amplitude of the electrogram signal of the arrhythmogenic signal at the region of the cardiac tissue undergoing ablation decreases after each iteration;
   wherein assessing the amplitude of an electrogram signal comprises measuring the amplitude during an intermission between the ablation pulses, and
   wherein the steps are performed automatically under a processor control.

2. The method according to claim 1, and comprising terminating the sequence of ablation pulses in response to detecting that the amplitude of the electrogram signal is below a predefined value.

3. The method according to claim 2, wherein the predefined value is equal to the predefined threshold.

4. The method according to claim 1, wherein assessing the amplitude of the electrogram signal comprises measuring the electrogram signal using a same electrodes used for applying the ablation pulses.

5. A system for iteratively estimating a thickness of cardiac tissue undergoing ablation, the system comprising:

an interface configured to output a sequence of ablation pulses applied by a probe to a region of the cardiac tissue, so as to create a lesion, by configuring the sequence such that a next incremental depth is smaller than a prespecified incremental value; and a processor, which is configured, for a given ablation pulse in the sequence, to:

estimate a current incremental depth added to the lesion due to the given ablation pulse;

estimate a cumulative depth of the lesion based on a prior cumulative depth prior to the given pulse, and on the current incremental depth;

assess an amplitude of an electrogram signal at the region of the cardiac tissue undergoing ablation after the probe applying the given ablation pulse, and, if the amplitude exceeds a predefined threshold, set an estimate of the thickness to be at least the cumulative depth; and set, for a next ablation pulse in the sequence of ablation pulses, an additional time duration for the next ablation where the additional time duration is configured to add an incremental lesion depth estimated to change a next incremental depth caused by the next ablation pulse to the region of the cardiac tissue, wherein the amplitude of the electrogram signal of the arrhythmogenic signal at the region of the cardiac tissue undergoing ablation decreases after each iteration, wherein the interface is configured to output irreversible electroporation (IRE) pulses, and wherein the processor is configured to assess the amplitude of an electrogram signal by measuring the amplitude during an intermission between the ablation pulses.

6. The system according to claim 5, wherein the processor is further configured to terminate the sequence of ablation pulses in response to detecting that the amplitude of the electrogram signal is below a predefined value.

7. The system according to claim 6, wherein the predefined value is equal to the predefined threshold.

8. The system according to claim 5, wherein the processor is configured to plan the sequence such that the next incremental depth is smaller than a prespecified incremental value.

9. The system according to claim 5, wherein the processor is further configured to assess the amplitude of the electrogram signal by measuring the electrogram signal using a same electrodes used for applying the ablation pulses.

* * * * *